US012423556B2

(12) United States Patent
Sakhinana et al.

(10) Patent No.: US 12,423,556 B2
(45) Date of Patent: Sep. 23, 2025

(54) MOLECULAR PROPERTY PREDICTION USING EDGE-INFORMATION FUSED GLOBAL GRAPH-READ NEURAL NETWORK FUNCTION

(71) Applicant: Tata Consultancy Services Limited, Mumbai (IN)

(72) Inventors: Sagar Srinivas Sakhinana, Pune (IN); Venkata Sudheendra Buddhiraju, Pune (IN); Sri Harsha Nistala, Pune (IN); Venkataramana Runkana, Pune (IN)

(73) Assignee: Tata Consultancy Services Limited, Mumbai (IN)

( * ) Notice: Subject to any disclaimer, the term of this patent is extended or adjusted under 35 U.S.C. 154(b) by 784 days.

(21) Appl. No.: 17/732,874

(22) Filed: Apr. 29, 2022

(65) Prior Publication Data
US 2023/0132463 A1    May 4, 2023

(30) Foreign Application Priority Data
Oct. 11, 2021    (IN) .............................. 202121046341

(51) Int. Cl.
G06N 3/044    (2023.01)
G16C 10/00    (2019.01)

(52) U.S. Cl.
CPC ............. *G06N 3/044* (2023.01); *G16C 10/00* (2019.02)

(58) Field of Classification Search
CPC ........ G06N 3/044; G06N 3/084; G06N 3/042; G06N 3/0442; G06N 3/0464; G06N 3/09; G16C 10/00; G16C 20/70; G16C 20/30
See application file for complete search history.

(56) References Cited

U.S. PATENT DOCUMENTS

2022/0188659 A1* 6/2022 Krasnoslobodtsev ......................
                                                      G16H 70/40
2023/0351215 A1* 11/2023 Sun ......................... G06N 5/022

OTHER PUBLICATIONS

Jo et al., "The message passing neural networks for chemical property prediction on SMILES," Methods, 179, 65-72 (2020).
Mercado et al., "Graph networks for molecular design," Mach. Learn.: Sci. Technol. 2: 025023 (2021).
Niu et al., "Permutation Invariant Graph Generation via Score-Based Generative Modeling," (2020).
(Continued)

*Primary Examiner* — Sanchita Roy
(74) *Attorney, Agent, or Firm* — Finnegan, Henderson, Farabow, Garrett & Dunner, LLP (57) ABSTRACT

This disclosure relates generally to system and method for molecular property prediction. The disclosed method includes mapping node embeddings of a molecular graph to a graph-level embedding characterizing the molecular graph. The graph level representation is acquired by pooling characteristics of hidden states of the nodes in the molecular graph by performing an iterative content based attention in a plurality of iterations. The content based attention is performed by considering an edge information fused transformed hidden state vector of the nodes of the molecular graph. The graph level embedding is fed through the linear projection to predict the molecular properties of the molecular graphs.

3 Claims, 5 Drawing Sheets

(56) References Cited

OTHER PUBLICATIONS

Withnall et al., "Building attention and edge message passing neural networks for bioactivity and physical-chemical property prediction," J Cheminform, 12:1 (2020).
Wu et al., "A Comprehensive Survey on Graph Neural Networks," Journal of Latex Class Files (2019).
Zhou et al., "Graph neural networks: A review of methods and applications," AI Open 1, pp. 57-81 (2020).

* cited by examiner

```
┌─────────────────────────────────────────────────────────┐
│ ACCESSING, VIA ONE OR MORE HARDWARE PROCESSORS, A       │
│ DATABASE COMPRISING A PLURALITY OF MOLECULAR GRAPHS     │
│ ASSOCIATED WITH A PLURALITY OF MOLECULES AND A          │─ 302
│ PLURALITY OF LABELS INDICATIVE OF CHEMICAL PROPERTIES OF│
│ THE PLURALITY OF THE MOLECULAR GRAPHS, WHEREIN EACH     │
│ MOLECULAR GRAPH OF THE PLURALITY OF MOLECULAR GRAPHS    │
│ COMPRISES A PLURALITY OF NODES AND A PLURALITY OF EDGES │
│ CONNECTING A PLURALITY OF NEIGHBORING NODES             │
└─────────────────────────────────────────────────────────┘
                            ↓
┌─────────────────────────────────────────────────────────┐
│ PROVIDING, VIA THE ONE OR MORE HARDWARE PROCESSORS,     │
│ EACH MOLECULAR GRAPH OF THE PLURALITY OF MOLECULAR      │
│ GRAPHS AS AN INPUT TO A MESSAGE PASSING PHASE OF A      │─ 304
│ MESSAGE PASSING NEURAL NETWORK (MPNN) TO EXCHANGE A     │
│ PLURALITY OF NEURAL MESSAGES OF THE MOLECULAR GRAPH,    │
│ WHEREIN EXCHANGING THE PLURALITY OF NEURAL MESSAGES     │
│ TRANSFORMS AND UPDATES EACH NODE EMBEDDING OF THE       │
│ EACH MOLECULAR GRAPH;                                   │
└─────────────────────────────────────────────────────────┘
                            ↓
┌─────────────────────────────────────────────────────────┐
│ MAP NODE EMBEDDINGS OF A MOLECULAR GRAPH FROM           │
│ AMONGST THE PLURALITY OF MOLECULAR GRAPHS TO A GRAPH-   │
│ LEVEL EMBEDDING CHARACTERIZING THE MOLECULAR GRAPH      │
│ VIA THE ONE OR MORE HARDWARE PROCESSORS, WHEREIN A      │
│ GRAPH LEVEL REPRESENTATION IS ACQUIRED BY POOLING       │
│ CHARACTERISTICS OF HIDDEN STATES OF THE NODES IN THE    │─ 306
│ MOLECULAR GRAPH BY PERFORMING AN ITERATIVE CONTENT      │
│ BASED ATTENTION IN A PLURALITY OF ITERATIONS            │
│ ┌─────────────────────────────────────────────────────┐ │
│ │ COMPUTE A QUERY VECTOR AT THE CURRENT ITERATION BY  │ │
│ │ AN LONG-SHORT-TERM-MEMORY (LSTM) MODEL USING AN     │ │
│ │ INPUT TO THE LSTM MODEL, A QUERY VECTOR AT A        │─ 308
│ │ PREVIOUS ITERATION STEP AND A WEIGHTED SUM OF A SET │ │
│ │ OF HIDDEN STATES OF EACH NODE FROM AMONGST A        │ │
│ │ PLURALITY OF NODES OF THE MOLECULAR GRAPH AT THE    │ │
│ │ PREVIOUS ITERATION STEP, WHEREIN THE QUERY VECTOR IS│ │
│ │ A LEARNABLE PARAMETER OF THE LSTM MODEL             │ │
│ └─────────────────────────────────────────────────────┘ │
└─────────────────────────────────────────────────────────┘
```

MOLECULAR PROPERTY PREDICTION USING EDGE-INFORMATION FUSED GLOBAL GRAPH-READ NEURAL NETWORK FUNCTION

PRIORITY CLAIM

This U.S. patent application claims priority under 35 U.S.C. § 119 to: India application No. 202121046341, filed on Oct. 11, 2021. The entire contents of the aforementioned application are incorporated herein by reference.

TECHNICAL FIELD

This disclosure relates generally to the field of molecular property prediction, and more particularly to system and method for molecular property prediction using edge-information fused global graph-read neural network function.

BACKGROUND

Machine learning techniques, in specific, supervised learning on drug-like potential molecules has remarkable applications for use in more effective drug discovery. These techniques provide substantial prospects in diminishing the computational complexity which is a key desideratum for prognostication of molecular properties and aid in cost reduction of developing a potential drug for treatment.

Message Passing Neural Networks (MPNN's) inspired by loopy belief propagation algorithm on a random graphical model is a graph-based property prediction framework. It leverages a message passing algorithm and a set-pooling aggregation operator to derive a graph-level representation of the complete input low treewidth chemical graphs to assist in inductive learning tasks. The MPNN's however suffer from inherent limitation to effectively encapsulate the characteristics of the molecular graph. Moreover, due to its high computational complexity, MPNN in not viable for real-time property prediction.

SUMMARY

Embodiments of the present disclosure present technological improvements as solutions to one or more of the above-mentioned technical problems recognized by the inventors in conventional systems. For example, in one embodiment, a processor implemented method for molecular property prediction is provided. The method includes accessing, via one or more hardware processors, a database comprising a plurality of molecular graphs associated with a plurality of molecules and a plurality of labels indicative of chemical properties of the plurality of the molecular graphs, wherein each molecular graph of the plurality of molecular graphs comprises a plurality of nodes and a plurality of edges connecting a plurality of neighboring nodes. Further, the method includes mapping node embeddings of a molecular graph from amongst the plurality of molecular graphs to a graph-level embedding characterizing the molecular graph via the one or more hardware processors, wherein a graph level embedding is acquired by pooling characteristics of hidden states of the nodes in the molecular graph by performing an iterative content based attention in a plurality of iterations. Pooling the characteristics of hidden states of the nodes in a current iteration step (at time t) of the plurality of iterations comprises computing a query vector at the current iteration by an Long-Short-Term-Memory (LSTM) model using an input to the LSTM model, the input includes a query vector at a previous iteration step (at time t−1) and a weighted sum of a set of hidden states of each node from amongst a plurality of nodes of the molecular graph at the previous iteration step, wherein the query vector is a learnable parameter of the LSTM model; and computing an attention score ($S_{i,t}$) based on an attention function computed at the current iteration step for each node of the plurality of nodes. Computing the attention score at each iteration comprises obtaining a linear projection of each tuple ($h_i^T$, $x_i^M$), wherein each tuple is represented as a concatenation of node-attributes, the node-attributes comprising the feature vector ($x_i^M$) of node i and hidden state vector ($h_i^T$) of the node i; and fusing edge information ($e_{j,i}^M$) with the node-attributes by taking a product of the linear projection with the edge information to obtain an edge information fused transformed hidden state vector of the node i. Further, the method comprises passing the edge information fused transformed hidden state vector of node i and the query vector to the attention function to compute the attention score ($S_{i,t}$); and determining an attention coefficient of the node using a softmax function, wherein the softmax function is computed using the attention score of node i with a set of neighboring nodes (j) of the node i. The method further comprises computing, via the one or more hardware processors, a weighted sum ($O_t$) of the node's hidden states at the current iteration step using the weighted sum ($O_t$) of the node's hidden states at the previous iteration step ($O_{t-1}$); obtaining a product of node's (i) hidden states from the plurality of iterations to compute a graph level embedding via the one or more hardware processors; and predicting the molecular properties of the molecular graphs via the one or more hardware processors by feeding the graph level embedding through the linear projection.

In another aspect, a system for molecular property prediction is provided. The system includes a memory storing instructions; one or more communication interfaces; and one or more hardware processors coupled to the memory via the one or more communication interfaces, wherein the one or more hardware processors are configured by the instructions to: access a database comprising a plurality of molecular graphs associated with a plurality of molecules and a plurality of labels indicative of chemical properties of the plurality of the molecular graphs, wherein each molecular graph of the plurality of molecular graphs comprises a plurality of nodes and a plurality of edges connecting a plurality of neighboring nodes. The one or more hardware processors are further configured by the instructions to map node embeddings of a molecular graph from amongst the plurality of molecular graphs to a graph-level embedding characterizing the molecular graph, wherein a graph level embedding is acquired by pooling characteristics of hidden states of the nodes in the molecular graph by performing an iterative content based attention in a plurality of iterations, wherein to pool the characteristics of hidden states of the nodes in a current iteration step (at time t) of the plurality of iterations, the one or more hardware processors are configured by the instructions to: compute a query vector at the current iteration by an Long-Short-Term-Memory (LSTM) model using an input to the LSTM model, the input includes a query vector at a previous iteration step (at time t−1) and a weighted sum of a set of hidden states of each node from amongst a plurality of nodes of the molecular graph at the previous iteration step, wherein the query vector is a learnable parameter of the LSTM model; compute an attention score ($S_{i,t}$) based on an attention function computed at the current iteration step for each node of the plurality of nodes. To compute the attention score at each iteration, the one or more hardware processors are configured by the instructions to obtain a linear projection of each tuple ($h_i^T$, $x_i^M$), wherein each tuple is represented as a concatenation of node-attributes, the node-attributes comprising the feature vector ($x_i^M$) of node i and hidden state vector ($h_i^T$) of the node i; and fuse edge information ($e_{j,i}^M$) with the node-attributes by taking a product of the linear projection with the edge information to obtain an edge information fused transformed hidden state vector of the node i. The one more hardware processors are further configured by the instructions to pass the edge information fused transformed hidden state vector of node i and the query vector to the attention function to compute the attention score ($S_{i,t}$). The one more hardware processors are further configured by the instructions to determine an attention coefficient of the node using a softmax function, wherein the softmax function is computed using the attention score of node i with a set of neighboring nodes (j) of the node i; compute a weighted sum ($\mathcal{O}_t$) of the node's hidden states at the current iteration step using the weighted sum ($\mathcal{O}_t$) of the node's hidden states at the previous iteration step ($\mathcal{O}_{t-1}$); obtain a product of node's hidden states from the plurality of iterations to compute a graph level embedding; and predict the molecular properties of the molecular graphs by feeding the graph level embedding through the linear projection.

In yet another aspect, a non-transitory computer readable medium for a method for molecular property prediction is provided. The non-transitory computer readable medium includes a plurality of instructions which when executed, cause the molecular property prediction via the following steps. Initially, a database is accessed that includes a plurality of molecular graphs associated with a plurality of molecules and a plurality of labels indicative of chemical properties of the plurality of the molecular graphs, wherein each molecular graph of the plurality of molecular graphs comprises a plurality of nodes and a plurality of edges connecting a plurality of neighboring nodes. The node embeddings of a molecular graph from amongst the plurality of molecular graphs are mapped to a graph-level embedding characterizing the molecular graph via the one or more hardware processors, wherein a graph level embedding is acquired by pooling characteristics of hidden states of the nodes in the molecular graph by performing an iterative content based attention in a plurality of iterations. Pooling the characteristics of hidden states of the nodes in a current iteration step (at time t) of the plurality of iterations comprises computing a query vector at the current iteration by an Long-Short-Term-Memory (LSTM) model using an input to the LSTM model, the input includes a query vector at a previous iteration step (at time t-1) and a weighted sum of a set of hidden states of each node from amongst a plurality of nodes of the molecular graph at the previous iteration step, wherein the query vector is a learnable parameter of the LSTM model; and computing an attention score ($S_{i,t}$) based on an attention function computed at the current iteration step for each node of the plurality of nodes. Computing the attention score at each iteration comprises obtaining a linear projection of each tuple ($h_i^T$, $x_i^M$), wherein each tuple is represented as a concatenation of node-attributes, the node-attributes comprising the feature vector ($x_i^M$) of node i and hidden state vector ($h_i^T$) of the node i; and fusing edge information ($e_{j,i}^M$) with the node-attributes by taking a product of the linear projection with the edge information to obtain an edge information fused transformed hidden state vector of the node i. Further, the method comprises passing the edge information fused transformed hidden state vector of node i and the query vector to the attention function to compute the attention score ($S_{i,t}$); and determining an attention coefficient of the node using a softmax function, wherein the softmax function is computed using the attention score of node i with a set of neighboring nodes (j) of the node i. A weighted sum ($\mathcal{O}_t$) of the node's hidden states at the current iteration step is computed using the weighted sum ($\mathcal{O}_t$) of the node's (i) hidden states at the previous iteration step ($\mathcal{O}_{t-1}$); a product of node's hidden states from the plurality of iterations is obtained to compute a graph level embedding; and the molecular properties of the molecular graphs is predicted by feeding the graph level embedding through the linear projection.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Convolution Neural Networks (CNNs) have contributed to a broad range of scientific breakthroughs, in the fields as deep residual learning for visual recognition, self-driving cars, optical character recognition engine, acoustic modeling in speech recognition, neural machine translation, etc. In view of the inherent methodology, CNN and its variant structured neural network architectures obtain dimensionality reduction and extract dominant features by performing spatial convolutions on Euclidean domains. The ConvNets input is obliged to, therefore, have a regular and grid-like structure. This restriction hampers the utilization of CNN's to numerous scientific disciplines, where irregular graph structure or manifold data are commonly accessible.

Chemical graph theory treats drug-like organic molecules as non-linear static graphs. Message Passing Neural Networks (MPNN) framework merges several distinct and unique contemporary models that exist in the literature. The MPNNs are an abstraction of a non-spectral approach based Graph Convolution Networks. The MPNNs operate on undirected chemical graphs, $\mathcal{G}^{\mathcal{M}} = (\mathcal{V}^{\mathcal{M}}, \varepsilon^{\mathcal{M}})$ Let $\mathcal{N}^{\mathcal{M}}$ ($|\mathcal{V}^{\mathcal{M}}|$) denote the number of nodes and E $^{\mathcal{M}}$ ($|\varepsilon^{\mathcal{M}}|$) represents the number of edges for a homogenous chemical graph, $\mathcal{G}^{\mathcal{M}}$. $\mathcal{G}^{\mathcal{M}}$ M is described by a set of node features, $N^{\mathcal{M}} \in \mathbb{R}^{|\mathcal{V}^{\mathcal{M}}| \times \mathbb{C}}$, $N_i^{\mathcal{M}} \in \mathbb{R}^{\mathbb{E} \times \mathbb{C}}$ $\forall i \in \mathcal{V}^{\mathcal{M}}$ and edge features $e_{ij}^{\mathcal{M}} \in \mathbb{R}^{|\mathbb{E}^{\mathcal{M}}| \times \mathbb{Z}}$, $\forall (i, j) \in \varepsilon^{\mathcal{M}}$. Here, i & j∈ $\mathcal{V}^{\mathcal{M}}$ refer to the neighboring nodes of the chemical graph and are connected by an arbitrary edge, $(i, j) \in \varepsilon^{\mathcal{M}} \leftrightarrow (j, i) \in \varepsilon^{\mathcal{M}}$, $\forall j \in \mathcal{N}$ (i). The chemical graph connectivity $\mathcal{G}^{\mathcal{M}} = (\mathcal{V}^{\mathcal{M}}, \varepsilon^{\mathcal{M}})$ is given by the adjacency matrix, $\mathcal{G} \mathcal{M}^{\mathcal{M}}$.

Molecules are represented as annotated undirected chemical graphs. The atoms are considered to be the nodes of the chemical graphs. The bonds connecting adjacent atoms in the chemical graphs correspond to edges. The MPNN framework is leveraged in this particular scientific discipline for mathematical modeling of the drug-like organic molecules. It helps to gain insight and assists in the description of the chemical graph's topology into a characteristic representation of the entire chemical graphs to later aid in the molecular property prediction task. Based on the graph's connectivity, an incident edge in between two neighboring atoms in the chemical compound (or nodes in a chemical graph) acts as both arriving and departing edge tagged by the same label (bond type).

Figure 1A:
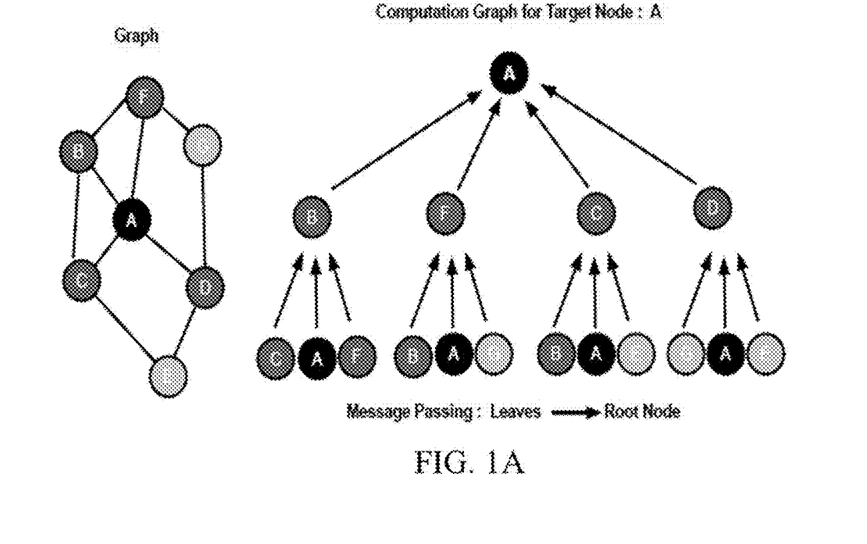
FIG. 1A illustrates a representation of message passing phase of a conventional message passing neural network (MPNN).
Figure 1B:
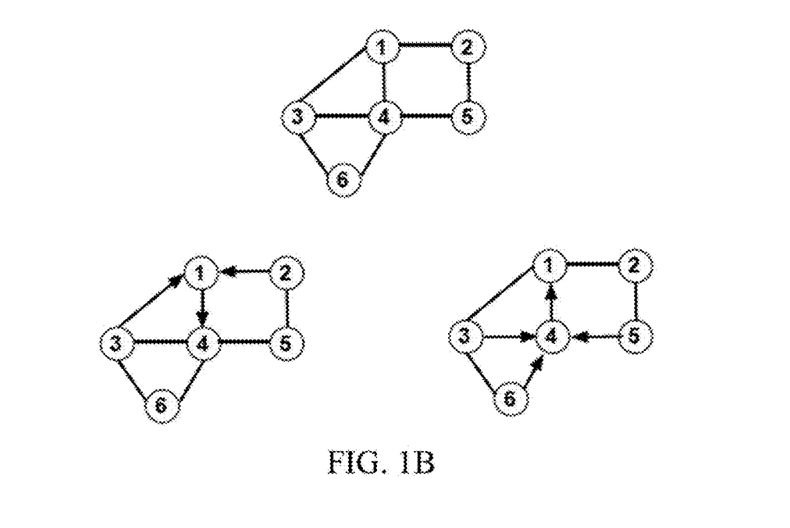
FIG. 1B illustrates a representation of readout phase of a conventional message passing neural network (MPNN).

The MPNNs forward pass consists of two phases—a message passing phase (illustrated in FIG. 1A) and a readout phase (illustrated in FIG. 1B). The message passing phase generates neural messages and update node representations by aggregating encoded information of node's embeddings from confined graph neighborhood. A permutation invariant readout phase is leveraged to perform graph pooling. Readout phase function takes an adjacency matrix $\mathcal{G}_A^{\mathcal{M}}$ as input and satisfies the following property, $\mathcal{M}(P\mathcal{G}_A^{\mathcal{M}} P^T) = \mathcal{M}(\mathcal{G}_A^{\mathcal{M}})$. Here, P is a permutation matrix. The message propagation utilizes the distinct message generating functions acting on the undirected chemical graph topology $M_{in}^f$ and $M_{out}^f$ represents the universal function approximator for the generation of neural messages received through a particular edge type and propagated from the same edge-type between the nodes of the chemical graphs, respectively. Based on the direction of the edge under consideration, that particular transformation function is put into operation on the edge, $e_{ji}^{\mathcal{M}}$. The MPNNs forward pass communicates messages as described by a computational graph for every target node from the bottom (leaf) node to the top (root) node by iterating for T computational time steps. These outgoing messages are evaluated for every edge by transforming the source node's hidden state according to the edge feature vector.

Identical edge-type incident on different node neighbors, which is characterized by distinct edge feature vectors share with the same instance of the message generating neural-network function. Each node in the molecular graph aggregates neural messages (message-pooling operation) from its local T-hop neighbors, as determined from GM and the received messages are perceived by the target node by performing mathematical computations to update its hidden representation. This message-passing scheme assists in learning effective discriminative hidden representations of the nodes in the chemical graphs, by adopting a Backpropagation through time (BPTT) learning algorithm for training the MPNNs framework when solved for graph-based inductive learning tasks. The MPNNs are synchronous message-passing systems. They update all messages in parallel. In the end, each edge between the vertices in the chemical graph have messages evaluated in both directions from the source to sink and contrariwise. The message passing phase is described by utilizing a message generating function, $M^f$, and node-embedding update neural network function, $V^f$. $M^f$ and $V^f$ might take possession of diverse in specific to be at variance with function settings. During the span of the message passing phase, the node-level embedding $h_i^t$ of every unique vertex in the molecular graph as given by its computational graph are overhauled and assembled on structural and feature information embedded messages $m_i^{t+1}$, received from its one-hop neighbors as depicted by, $$m_i^{t+1} = \sum_{j \in N(i)} M^f(h_j^t, e_{ji}^{\mathcal{M}}) \quad (1)$$

$$h_i^{t+1} = V^f(h_i^t, m_i^{t+1}) \quad (2)$$

Here, $\Sigma_{j \in N(i)}$ depicts the aggregation of neural-information embedded messages over the local one-hop neighborhood of the node, $i \in \mathcal{V}^{\mathcal{M}}$ in the chemical graph, $\mathcal{G}^{\mathcal{M}}$. Here, $h_i$ is learned with the MPNN model parameters through a representative function of the entire input graph when solved for addressing supervised graph regression tasks such as molecular graph property prediction. The readout phase of the MPNN framework performs graph-pooling through set-pooling approach by determining a discriminative graph embedding for the entire input molecular graph by utilizing a differentiable node-reordering invariant neural network function, $R^f$ according to, $\hat{y} = R^f(\{h_i^T | i \in \mathcal{V}^{\mathcal{M}}(\mathcal{G}^{\mathcal{M}})\})$. $M^f$, $V^f$, and $R^f$ are differentiable neural network functions and have learnable parameters. Mini-Batching with an MPNN with batch size as a hyper-parameter results in the faster training and augments performance of the graph-based deep learning algorithm. It is viable here in this context as it initiates and propagates neural messages across several molecular graphs with varying numbers of vertices $|\mathcal{V}^{\mathcal{M}}|$ and $|\varepsilon^{\mathcal{M}}|$. The feature representation of the vertices in the molecular graph, $\mathcal{G}^{\mathcal{M}}$ is denoted by, data.x. data.edgeindex describes the edge indices of source and sink vertices of the edge under consideration and vice-versa. data.edgeattr represents the static edge attributes. data.y is the pre-determined DFT-evaluated properties (ground-truth) for the chemical graphs. The discrepancy between the MPNN model output (estimated) and the true values are measured by the mean-squared error loss function for this graph-based supervised regression task. The Edge-Conditioned Convolution Networks (ECCN) is described by, $h_i^{t+1} = \Lambda h_i^t + \Sigma_{j \in N(i)} h_j^t \cdot \Omega_\Lambda(e_{ij}^{\mathcal{M}})$ Here, $\Omega_\Lambda$ denotes a multilayer perceptron, parameterized by $\Lambda$. The aggregated vector message perceived by the sink node, i is described by $m_i^{t+1} = \Sigma_{j \in N(i)} h_j^t \cdot \Omega_\Lambda(e_{ij}^{\mathcal{M}})$. The MPNN framework message-generating neural-network function is described by, $M^f(h_j^t, e_{ij}^{\mathcal{M}}) = h_j^t \cdot \Omega_\Lambda(e_{ij}^{\mathcal{M}})$. The vertex update function is described by, $V^f(h_i^t, m_i^{t+1})$:GRU ($h_i^t$, $m_i^{t+1}$). Here, GRU is a known Gated Recurrent Unit. The hidden state of the previous state is given by, $V^f(h_i^t, m_i^{t+1}):GRU(h_i^t, m_i^{t+1})$.

Here, n denotes the total number of nodes in the chemical graphs in a given batch size. $d_m$ & $d_n$ are the characteristic dimension of neural messages and node attributes respectively. Here, the reset gate, $R_t$, $Z_t$, $h_i^t$, $\tilde{h}_i^t$ are evaluated as, $$R_t = \sigma(m_i^{t+1} W_r + h_i^t W_{rh} + b_r), \quad (3)$$

$$Z_t = \sigma(m_i^{t+1} W_z + h_i^t W_{zh} + b_z) \quad (4)$$

$$\tilde{h}_i^t = \tanh(m_i^{t+1} W_{\tilde{h}} + (R_t \odot h_i^t) W_{hh} + b_h) \quad (5)$$

$$h_i^{t+1} = Z_t \odot h_i^t + (1 - Z_t) \odot \tilde{h}_i^t \quad (6)$$

Here, $W_r$, $W_z$, $W_{\tilde{h}} \in \mathbb{R}^{d_m \times d_h}$, $W_{rh}$, $W_{zh}$, $W_{hh} \in \mathbb{R}^{d_h \times d_h}$ are the weight parameters, $b_r$, $b_z$, $b_h \in \mathbb{R}^{1 \times d_h}$ are the bias.

The graph-level global pooling neural network is evaluated as $$\hat{y} = R^f(\{h_i^T \mid i \in \mathcal{V}^M(\mathcal{G}^M)\}) : Set2Set(\{h_i^T \mid i \in \mathcal{V}^M(\mathcal{G}^M)\}) \quad (7)$$

The MPNN however leads to over-smoothing of learnable embeddings for vertices with higher valency. Various embodiments described herein provides a method and system for molecular property prediction using an Edge-Conditioned Graph Pooling Layer. The disclosed system is resilient to noise by learning to adapt to kingpin on the task-relevant fragment of the molecular graphs at varying receptive fields, locality, and depth to augment the discriminative power of node and graph-level embeddings. The disclosed method learns the expressive/discriminative node and graph level embeddings to aid in molecular property prediction with a reduced computational complexity.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Referring now to the drawings, and more particularly to FIG. 2 through 5, where similar reference characters denote corresponding features consistently throughout the figures, there are shown preferred embodiments and these embodiments are described in the context of the following exemplary system and/or method.

Figure 2:
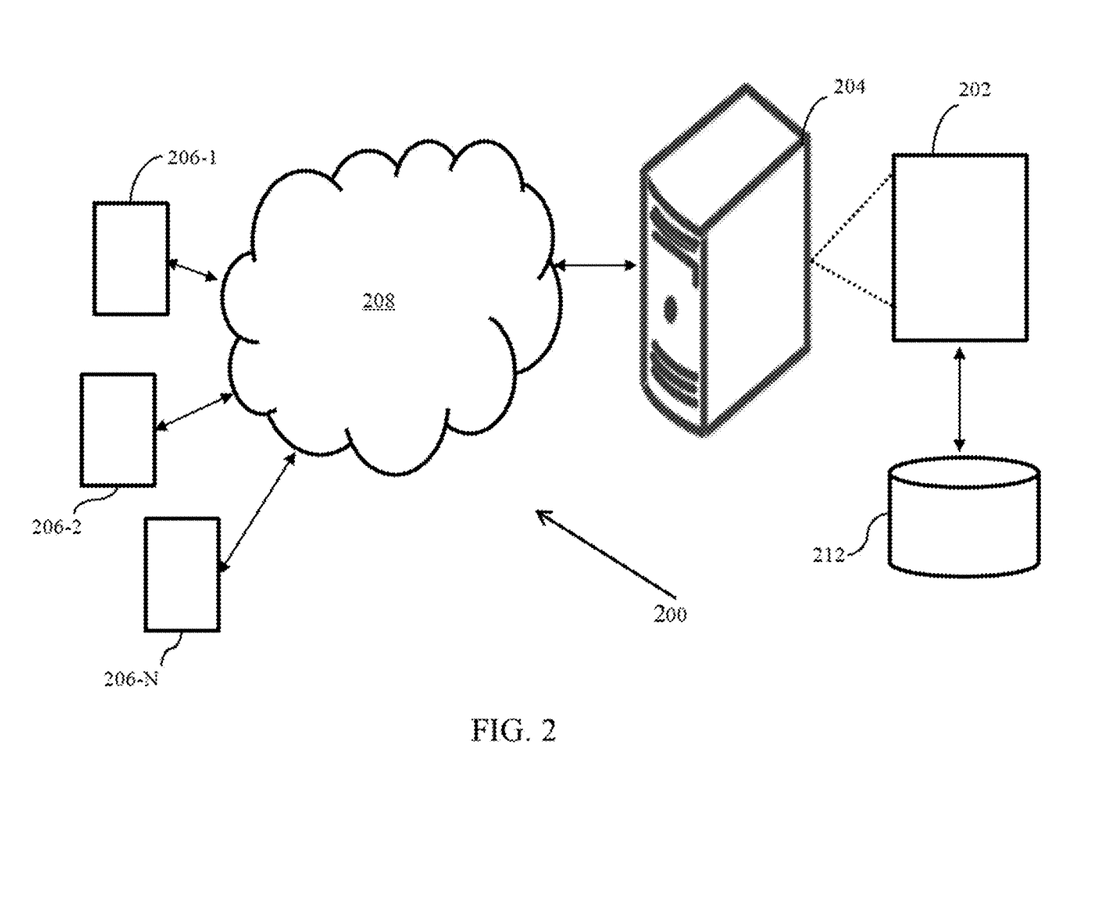
FIG. 2 illustrates a network implementation of a system for molecular property prediction using edge-information fused global graph-read neural network function according to some embodiments of the present disclosure.

FIG. 2 illustrates a network implementation 200 of a system for molecular property prediction according to some embodiments of the present disclosure. The disclosed system provides a supervised learning on drug-like potential molecules for use in effective drug discovery. It provides substantial prospects in diminishing the computational complexity which is a key desideratum for prognostication of molecular properties and aid in billion price tag cost reduction of developing a potential drug for treatment.

The proposed system comprises of message-passing, vertex update and graph-pooling modules which augment the graph-level prediction tasks accuracy by taking into account the structure of the graph. The proposed novel design of message-passing pipeline augments the graph-level prediction tasks accuracy by taking into account the structure of the graph.

Although the present disclosure is explained considering that the system 202 is implemented on a server, it may be understood that the system 202 may also be implemented in a variety of computing systems 204, such as a laptop computer, a desktop computer, a notebook, a workstation, a cloud-based computing environment and the like. It will be understood that the system 202 may be accessed through one or more devices 206-1, 206-2 . . . 206-N, collectively referred to as devices 206 hereinafter, or applications residing on the devices 206. Examples of the devices 206 may include, but are not limited to, a portable computer, a personal digital assistant, a handheld device, a smartphone, a tablet computer, a workstation and the like. The devices 206 are communicatively coupled to the system 202 through a network 208.

In an embodiment, the network 208 may be a wireless or a wired network, or a combination thereof. In an example, the network 208 can be implemented as a computer network, as one of the different types of networks, such as virtual private network (VPN), intranet, local area network (LAN), wide area network (WAN), the internet, and such. The network 206 may either be a dedicated network or a shared network, which represents an association of the different types of networks that use a variety of protocols, for example, Hypertext Transfer Protocol (HTTP), Transmission Control Protocol/Internet Protocol (TCP/IP), and Wireless Application Protocol (WAP), to communicate with each other. Further, the network 208 may include a variety of network devices, including routers, bridges, servers, computing devices, storage devices. The network devices within the network 208 may interact with the system 202 through communication links.

As discussed above, the system 202 may be implemented in a computing device 204, such as a hand-held device, a laptop or other portable computer, a tablet computer, a mobile phone, a PDA, a smartphone, and a desktop computer. The system 202 may also be implemented in a workstation, a mainframe computer, a server, and a network server. In an embodiment, the system 202 may be coupled to a data repository, for example, a repository 212. The repository 212 may store data processed, received, and generated by the system 202. In an alternate embodiment, the system 202 may include the data repository 212.

The network implementation 200 supports various connectivity options such as BLUETOOTH®, USB, ZigBee and other cellular services. The network environment enables connection of devices 206 such as Smartphone with the server 204, and accordingly with the database 212 using any communication link including Internet, WAN, MAN, and so on. In an exemplary embodiment, the system 202 is implemented to operate as a stand-alone device. In another embodiment, the system 202 may be implemented to work as a loosely coupled device to a smart computing environment.

Figure 3A:
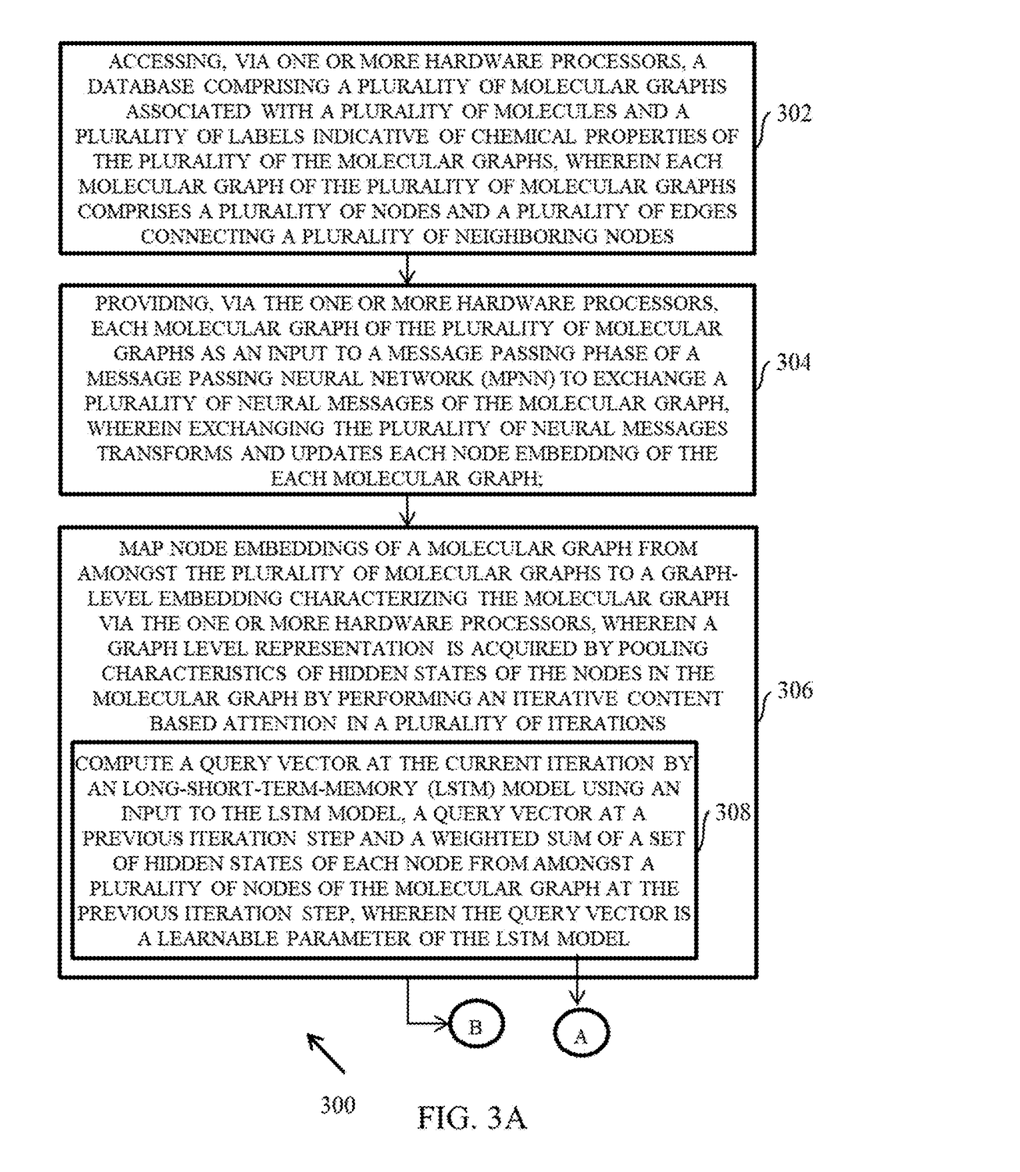
FIGS. 3A and 3B is a flow diagram illustrating a method for molecular property prediction using edge-information fused global graph-read neural network function in accordance with some embodiments of the present disclosure.
Figure 3B:
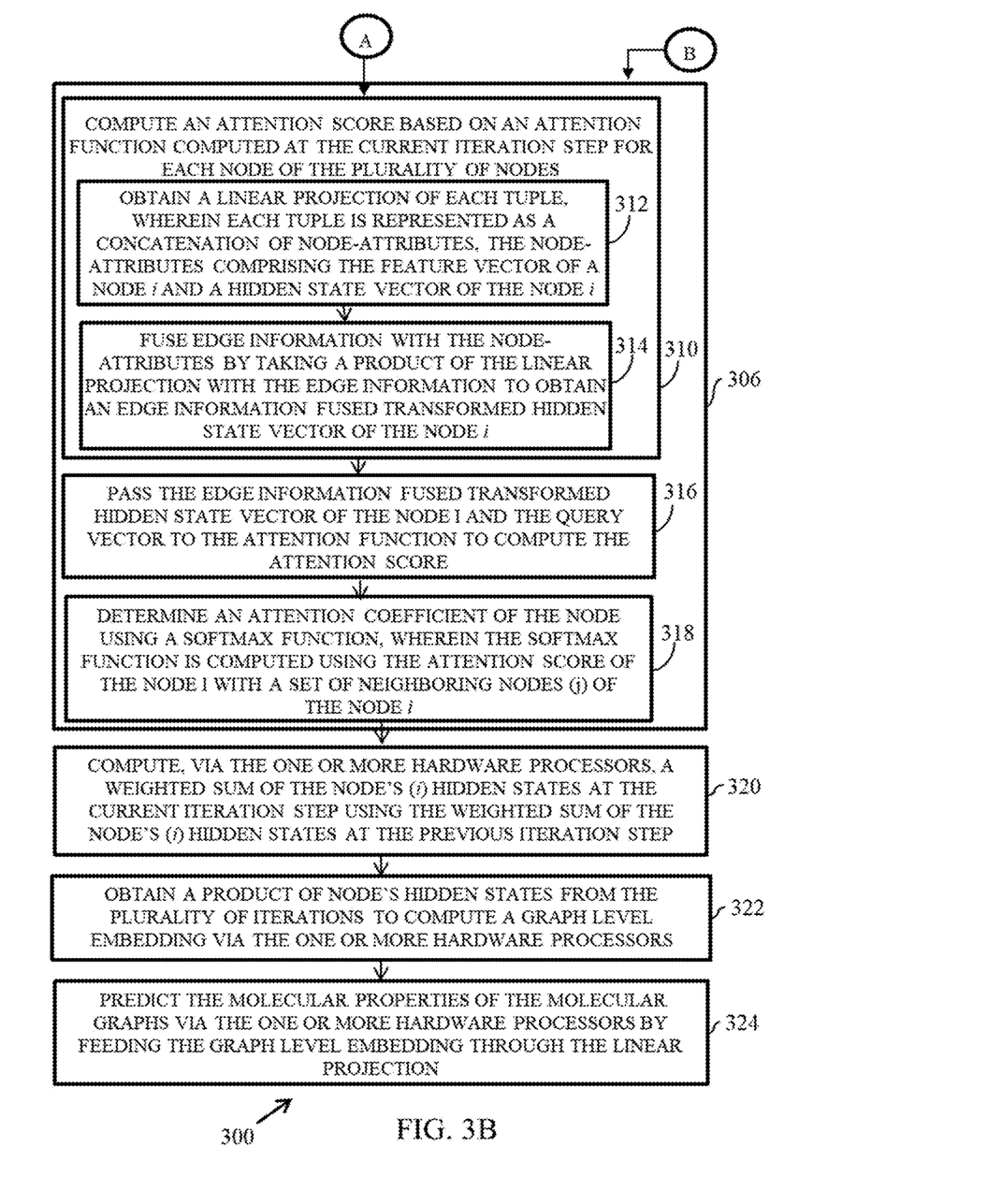

FIGS. 3A and 3B illustrate a flow chart of a method 300 for molecular property prediction using edge-information fused global graph-read neural network function, in accordance with an example embodiment of present disclosure.

Operations of the flowchart, and combinations of operation in the flowchart, may be implemented by various means, such as hardware, firmware, processor, circuitry and/or other device associated with execution of software including one or more computer program instructions. For example, one or more of the procedures described in various embodiments may be embodied by computer program instructions. In an example embodiment, the computer program instructions, which embody the procedures, described in various embodiments may be stored by at least one memory device of a system and executed by at least one processor in the system. Any such computer program instructions may be loaded onto a computer or other programmable system (for example, hardware) to produce a machine, such that the resulting computer or other programmable system embody means for implementing the operations specified in the flowchart. It will be noted herein that the operations of the method 300 are described with help of system 202. However, the operations of the method 300 can be described and/or practiced by using any other system.

At step 302 of method 300, a database comprising a plurality of molecular graphs associated with a plurality of molecules is accessed, via one or more hardware processors. The database further includes a plurality of labels indicative of chemical properties of the plurality of the molecular graphs. Each molecular graph of the plurality of molecular graphs includes a plurality of nodes and a plurality of edges connecting a plurality of neighboring nodes from amongst the plurality of nodes. For example, the database may include annotated independent and identically distributed molecular graphs, $D^{\mathcal{M}} = (G_1^{\mathcal{M}}, y_1^{\mathcal{M}}), (G_1^{\mathcal{M}}, y_1^{\mathcal{M}}) \ldots (G_{|D|}^{\mathcal{M}}, y_{|D|}^{\mathcal{M}})$ Here, $y_i^{\mathcal{M}}$ are the associated chemical properties corresponding to the molecular graph, $\mathcal{G}_A^{\mathcal{M}}$. The objective of the graph-based molecular property prediction framework is by operating on the topology of the molecular graphs described by a set of node features, $N^{\mathcal{M}} \in \mathbb{R}^{|\mathcal{V}^{\mathcal{M}}| \times \mathbb{C}}$ and static edge features, $e_{ij}^{\mathcal{M}} \in \mathbb{R}^{|\mathcal{E}^{\mathcal{M}}| \times \mathbb{Z}}, \forall (i, j) \in \mathcal{E}^{\mathcal{M}}$ is to learn a novel mapping $f: \mathcal{G}^{\mathcal{M}} \to h_k^{\mathcal{M}}, \forall k \in \mathcal{V}^{\mathcal{M}} \to h\mathcal{G}^{\mathcal{M}} \to y_i^{\mathcal{M}}$ that maps molecular graphs structure to the set of labels. $h_k^{\mathcal{M}}$ is the learned hidden representation vector of node k. Here, $y_i^{\mathcal{M}}$ denotes the target molecular properties.

As previously discussed, the MPNN pipeline operates on annotated molecular graphs in two subsequent phases, the message passing phase characterized by $\mathcal{M}\mathcal{G}, \mathcal{M}\mathcal{G}\mathcal{G}$, UPD neural-network functions and the readout phase characterized by global-pooling operator, $R^f$. The selection of a function setting for a set-aggregator, $R^f$ is of paramount importance, as it should allow invariance to the MPNN model output to the order of selection of the node-level embeddings. The objective of a set pooling function, $R^f$ is to map the graph's node-level embeddings to a graph-level embedding $\{h_1^T, \ldots, h_{|v|}^T\}$, which characterizes the entire input molecular graph. The graph-level representation is acquired by utilizing the structure of the molecular graph similar to graph clustering or coarsening pooling operations. It leverages extended memory recurrent neural networks and attention mechanism to pool the characteristic hidden states of the vertices in the graph. It is driven by a mechanism of iterative content-based attention.

At 304, the method 300 includes mapping molecular graph's node embeddings to a graph-level embedding $h\mathcal{G}$ characterizing the input molecular graph. The graph level representation is acquired by pooling characteristics of hidden states of the nodes in the molecular graph by performing an iterative content-based attention in a plurality of iterations (M). Herein, pooling the characteristics of hidden states of the nodes in an iteration of the plurality of iterations is described further with reference to steps 306-316.

At 306, the method 304 includes computing a query vector ($Q_t$) at a current iteration by an Long-Short-Term-Memory (LSTM) model using an input to the LSTM model, a query vector ($Q_{t-1}$) at a previous iteration step (t-1) and a weighted sum ($O_{t-1}$) of a set of hidden states of each node from amongst a plurality of nodes of the molecular graph at the previous iteration step. Herein, the query vector is a learnable parameter of the LSTM model. The query vector at the current iteration step, t is denoted as:

$$Q_t = LSTM(O_{t-1}, Q_{t-1})$$

At 308, the method 304 includes computing an attention score $S_{i,t}$ based on an attention function $f_a$ computed at the current iteration step for each node of the plurality of nodes. Herein, it will be understood that the attention function is evaluated at every intermediate iteration-step, t for each node, i. The method for computing the attention score at each iteration is described with reference to steps 310-316. At step 310, the method 308 includes obtaining a linear projection $\Theta[h_i^T \| x_i^{\mathcal{M}}]$ of each tuple $(h_i^T, x_i^{\mathcal{M}})$. Herein, each tuple is represented as a concatenation of node-attributes. The node-attributes includes the feature vector of node i and hidden state vector of node i. The edge information $e_{j,i}^{\mathcal{M}}$ is fused with the node-attributes at step 312 by taking a product of the linear projection $\Theta[h_i^T \| x_i^{\mathcal{M}}]$ with the edge information $e_{j,i}^{\mathcal{M}}$ to obtain an edge information fused transformed hidden state vector of the node i.

At step 314, the method 308 includes passing the edge information fused transformed hidden state vector of node i and the query vector to the attention function to compute the attention score.

$$S_{i,t} = f_a(e_{j,i}^{\mathcal{M}} \cdot \Theta[h_i^T \| x_i^{\mathcal{M}}], Q_t), \forall i \in \mathcal{V}^{\mathcal{M}}$$

$x_i^{\mathcal{M}}$ ($h_i^0$)=$x_i^{\mathcal{M}}$) denotes the feature vector of the node.

At step 316, the method 308 includes determining an attention coefficient of the node using the softmax function. The softmax function is computed using the attention score of node i with a set of neighboring nodes of the node i. as shown below:

$$a_{i,t} = \frac{\exp(s_{i,t})}{\sum_{j \in \mathcal{V}^{\mathcal{M}}} \exp(s_{j,t})}, \forall i \in \mathcal{V}^{\mathcal{M}}$$

The softmax function is leveraged to determine the attention coefficients of node, i at each iteration t.

At step 318, the method includes computing a weighted sum of the node's hidden states at the current iteration step using the weighted sum of the node's hidden states.

$$O_t = \sum_{i \in \mathcal{V}^{\mathcal{M}}} a_{i,t}(e_{j,i}^{\mathcal{M}} \cdot \Theta[h_i^T \| x_i^{\mathcal{M}}])$$

At step 320, the method includes obtaining a product of node's hidden states from the plurality of iterations to compute a graph level embedding. The graph-level embedding is determined as:

$$h_M^* = O_1 \odot O_2 \odot \ldots \odot O_M$$

The embedding $h_M^*$ is fed through a downstream multi-layer perceptron neural network to predict the molecular properties of the chemical graphs. Here, $\odot$ denotes element-wise multiplication. Then the graph level embedding, $h^{\mathcal{M}}*$ from the graph-topology aware variant of the global graph-read neural net function is immutable to the reordering of the tuples T. At step 322, the method includes feeding the graph level embedding through the linear projection to predict the molecular properties of the molecular graphs. In an embodiment, the set2set algorithm may be utilized for determining the molecular properties using the linear layer from the graph level embedding of the molecular graph. An example algorithm illustrating steps of the proposed method is presented below:

Require: Molecular Graph GM, Node Feature & Static Edge-Feature Matrix
Ensure: T-hop, local-graph neighborhood aggregation
Message-Passing Phase
for t∈ [T] do
  #Propagate messages
  for i∈ $\mathcal{V}^{\mathcal{M}}$ ($\mathcal{G}^{\mathcal{M}}$) do
    for j∈ $\mathcal{N}$ i do $$\phi_{j \to i}^{(t)} = \mathcal{MG}\left(h_j^{(t-1)}, e_{ji}^{\mathcal{M}}\right)$$

end for
  end for
  #Update vertex hidden states
  for I∈ $\mathcal{V}^{\mathcal{M}}$ ($\mathcal{G}^{\mathcal{M}}$) do $$h_i^{(t)} = \mathcal{UPD}\left(h_i^{(t-1)}, \mathcal{AGG}_{j \in \mathcal{N}i} \phi_{j \to i}^{(t)}\right)$$

end for
end for
Graph-level Embedding $$h_{\mathcal{G}^{\mathcal{M}}} = R^f\left(\{h_i^T\}, \forall j \in \mathcal{V}^{\mathcal{M}}(\mathcal{G}^{\mathcal{M}})\right)$$

Return Graph-level embedding, $h_{\mathcal{G}}^{\mathcal{M}}$.

Figure 4:
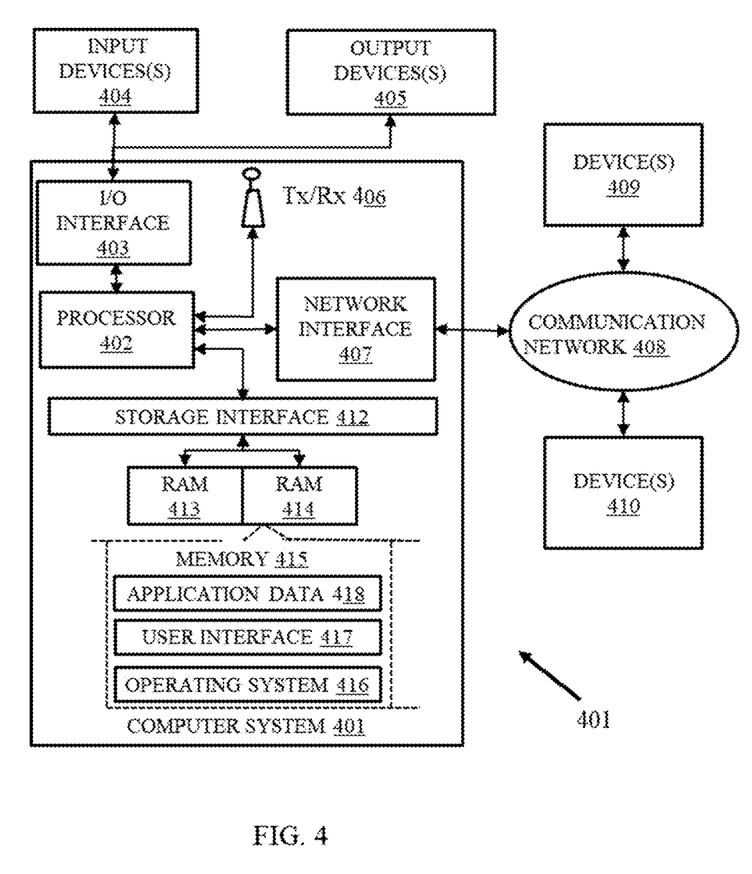
FIG. 4 is a block diagram of an exemplary computer system for implementing embodiments consistent with the present disclosure.

FIG. 4 is a block diagram of an exemplary computer system 401 for implementing embodiments consistent with the present disclosure. The computer system 401 may be implemented in alone or in combination of components of the system 202 (FIG. 2). Variations of computer system 401 may be used for implementing the devices included in this disclosure. Computer system 401 may comprise a central processing unit ("CPU" or "hardware processor") 402. The hardware processor 402 may comprise at least one data processor for executing program components for executing user- or system-generated requests. The processor may include specialized processing units such as integrated system (bus) controllers, memory management control units, floating point units, graphics processing units, digital signal processing units, etc. The processor may include a microprocessor, such as AMD Athlon™, Duron™ or Opteron™, ARM's application, embedded or secure processors, IBM PowerPC™, Intel's Core, Itanium™, Xeon™, Celeron™ or other line of processors, etc. The processor 402 may be implemented using mainframe, distributed processor, multi-core, parallel, grid, or other architectures. Some embodiments may utilize embedded technologies like application specific integrated circuits (ASICs), digital signal processors (DSPs), Field Programmable Gate Arrays (FPGAs), etc. The processor 402 may be a multi-core multi-threaded processor.

Processor 402 may be disposed in communication with one or more input/output (I/O) devices via I/O interface 403. The I/O interface 403 may employ communication protocols/methods such as, without limitation, audio, analog, digital, monoaural, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.11 a/b/g/n/x, Bluetooth, cellular (e.g., code-division multiple access (CDMA), high-speed packet access (HSPA+), global system for mobile communications (GSM), long-term evolution (LTE), WiMax, or the like), etc.

Using the I/O interface 403, the computer system 401 may communicate with one or more I/O devices. For example, the input device 404 may be an antenna, keyboard, mouse, joystick, (infrared) remote control, camera, card reader, fax machine, dongle, biometric reader, microphone, touch screen, touchpad, trackball, sensor (e.g., accelerometer, light sensor, GPS, gyroscope, proximity sensor, or the like), stylus, scanner, storage device, transceiver, video device/source, visors, etc.

Output device 405 may be a printer, fax machine, video display (e.g., cathode ray tube (CRT), liquid crystal display (LCD), light-emitting diode (LED), plasma, or the like), audio speaker, etc. In some embodiments, a transceiver 406 may be disposed in connection with the processor 402. The transceiver may facilitate various types of wireless transmission or reception. For example, the transceiver may include an antenna operatively connected to a transceiver chip (e.g., Texas Instruments WiLink WL1283, Broadcom BCM4750IUB8, Infineon Technologies X-Gold 618-PMB9800, or the like), providing IEEE 802.11a/b/g/n, Bluetooth, FM, global positioning system (GPS), 2G/3G HSDPA/HSUPA communications, etc.

In some embodiments, the processor 402 may be disposed in communication with a communication network 408 via a network interface 507. The network interface 407 may communicate with the communication network 508. The network interface may employ connection protocols including, without limitation, direct connect, Ethernet (e.g., twisted pair 10/100/1000 Base T), transmission control protocol/internet protocol (TCP/IP), token ring, IEEE 802.11a/b/g/n/x, etc. The communication network 408 may include, without limitation, a direct interconnection, local area network (LAN), wide area network (WAN), wireless network (e.g., using Wireless Application Protocol), the Internet, etc. Using the network interface 407 and the communication network 408, the computer system 401 may communicate with devices 409 and 410. These devices may include, without limitation, personal computer(s), server(s), fax machines, printers, scanners, various mobile devices such as cellular telephones, smartphones (e.g., Apple iphone, Blackberry, Android-based phones, etc.), tablet computers, eBook readers (Amazon Kindle, Nook, etc.), laptop computers, notebooks, gaming consoles (Microsoft Xbox, Nintendo DS, Sony PlayStation, etc.), or the like. In some embodiments, the computer system 401 may itself embody one or more of these devices.

In some embodiments, the processor 402 may be disposed in communication with one or more memory devices (e.g., RAM 413, ROM 414, etc.) via a storage interface 412. The storage interface may connect to memory devices including, without limitation, memory drives, removable disc drives, etc., employing connection protocols such as serial advanced technology attachment (SATA), integrated drive electronics (IDE), IEEE-1394, universal serial bus (USB), fiber channel, small computer systems interface (SCSI), etc. The memory drives may further include a drum, magnetic disc drive, magneto-optical drive, optical drive, redundant array of independent discs (RAID), solid-state memory devices, solid-state drives, etc. Variations of memory devices may be used for implementing, for example, any databases utilized in this disclosure.

The memory devices may store a collection of programs or database components, including, without limitation, an operating system 416, user interface application 417, user/application data 418 (e.g., any data variables or data records discussed in this disclosure), etc. The operating system 416 may facilitate resource management and operation of the computer system 401. Examples of operating systems include, without limitation, Apple Macintosh OS X, Unix, Unix-like system distributions (e.g., Berkeley Software Distribution (BSD), FreeBSD, NetBSD, OpenBSD, etc.), Linux distributions (e.g., Red Hat, Ubuntu, Kubuntu, etc.), IBM OS/2, Microsoft Windows (XP, Vista/7/8, etc.), Apple IOS, Google Android, Blackberry OS, or the like. User interface 417 may facilitate display, execution, interaction, manipulation, or operation of program components through textual or graphical facilities. For example, user interfaces may provide computer interaction interface elements on a display system operatively connected to the computer system 401, such as cursors, icons, check boxes, menus, scrollers, windows, widgets, etc. Graphical user interfaces (GUIs) may be employed, including, without limitation, Apple Macintosh operating systems' Aqua, IBM OS/2, Microsoft Windows (e.g., Aero, Metro, etc.), Unix X-Windows, web interface libraries (e.g., ActiveX, Java, Javascript, AJAX, HTML, Adobe Flash, etc.), or the like.

In some embodiments, computer system 401 may store user/application data 418, such as the data, variables, records, etc. as described in this disclosure. Such databases may be implemented as fault-tolerant, relational, scalable, secure databases such as Oracle or Sybase. Alternatively, such databases may be implemented using standardized data structures, such as an array, hash, linked list, structured text file (e.g., XML), table, or as hand-oriented databases (e.g., using HandStore, Poet, Zope, etc.). Such databases may be consolidated or distributed, sometimes among various computer systems discussed above. It is to be understood that the structure and operation of any computer or database component may be combined, consolidated, or distributed in any working combination.

Additionally, in some embodiments, (the server, messaging and instructions transmitted or received may emanate from hardware, including operating system, and program code (i.e., application code) residing in a cloud implementation. Further, it should be noted that one or more of the systems and methods provided herein may be suitable for cloud-based implementation. For example, in some embodiments, some or all of the data used in the disclosed methods may be sourced from or stored on any cloud computing platform.

Example

For the purpose of validation, experiments were conducted using QM-9 data set. The model (as implemented by the disclose system) was trained for graph-level-based regression tasks for the Quantum Chemistry property prediction task. Message passing computational steps, T was constrained to be at 3. The set2set mathematical iterations, M was on par with T. Here, the model trained by leveraging a random selection of datasets for stochastic gradient descent optimization with the Adaptive Moment Estimation optimizer algorithm, with batch size 10. The number of iterations (epochs) is 100 cycles through the full training dataset. The beginning learning rate was chosen as $1e^{-3}$. The learning rate was decayed at 51st epoch by half and maintained it constant in the span of [51; 75] epochs throughout the training and the beginning step size learning rate l decayed to a terminating learning rate $2.5e^{-4}$, using a decay factor by 4 in the range [76; 100] epochs. The QM-9 dataset consists of approximately 134K molecules. The validation set comprises 10000 samples. The test set is composed of 10000 samples and the remaining are for the training set. Here, early stopping is implemented on the validation dataset to prevent the model from over-fitting and for model selection. Finally, the performance of the model was evaluated and the evaluation metric based totally on the test set was published. Feature scaling was performed on the target properties to be predicted. Z-score normalization is leveraged to have distribution mean zero and the expectation of the squared deviation to one for each target property. The gradient descent (aka back-propagation) algorithm was run in weight space by updating the parameters according to the gradients of the loss function, the mean squared error between the predicted model outputs and the predetermined DFT properties. The results are reported in MAE metric in table 1 below.

TABLE

Performance comparison of the disclosed method with the baseline algorithms on test dataset

| Target | Unit | PPGN | SchNet | PhysNet | MEGNet-S | Comorant | DimeNet | EC-GRNN |
|---|---|---|---|---|---|---|---|---|
| Cv | Cal/(mol K) | 0.055 | 0.033 | 0.0529 | 0.05 | 0.13 | 0.0286 | 0.0133 |
| G | meV | 36.4 | 14 | 9.4 | 12 | — | 8.98 | 0.0464 |
| H | meV | 36.3 | 14 | 8.42 | 12 | — | 8.11 | 0.0167 |
| HOMO | meV | 40.3 | 41 | 32.9 | 43 | 36 | 27.8 | 0.0194 |
| LUMO | meV | 32.7 | 34 | 24.7 | 44 | 36 | 19.7 | 0.0162 |
| R2 | Bohr2 | 0.592 | 0.073 | 0.765 | 0.302 | 0.673 | 0.331 | 0.0291 |
| U | meV | 36.8 | 14 | 8.15 | 12 | — | 7.89 | 0.0827 |
| U0 | meV | 36.8 | 14 | 8.15 | 12 | — | 8.02 | 0.0184 |
| ZPVE | meV | 3.12 | 1.7 | 1.39 | 1.43 | 1.98 | 1.29 | 0.0000531 |
| alpha | Bohr3 | 0.131 | 0.235 | 0.0615 | 0.081 | 0.092 | 0.0469 | 0.0813 |
| gap | meV | 60 | 63 | 42.5 | 66 | 60 | 34.8 | 0.0812 |
| mu | D | 0.047 | 0.033 | 0.0529 | 0.05 | 0.13 | 0.0286 | 0.0609 |

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

Various embodiments described herein method and system for molecular property predictions. The disclosed message-passing pipeline in the MPNN foster family is trained by learning end-to-end. The proposed pipeline provides an effective algorithm (for example, Algorithm 1 given below) for learning the discriminative node embeddings of the arbitrary sized, non-linear chemical graph-structured data by utilizing the relational inductive biases that are shared across the non-Euclidean graph domain. These pipeline formalism variants driven by inductive learning tasks are leveraged for the molecular graphs properties prediction.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor-implemented method, comprising:

accessing, via one or more hardware processors, a database comprising a plurality of molecular graphs associated with a plurality of molecules and a plurality of labels indicative of chemical properties of the plurality of the molecular graphs, wherein each molecular graph of the plurality of molecular graphs comprises a plurality of nodes and a plurality of edges connecting a plurality of neighboring nodes;

mapping a node embedding of a molecular graph from amongst the plurality of molecular graphs to a graph-level embedding characterizing the molecular graph, via the one or more hardware processors, wherein the graph level embedding is acquired by pooling characteristics of hidden states of the nodes in the molecular graph by performing an iterative content based attention in a plurality of iterations, wherein pooling the characteristics of hidden states of the nodes in a current iteration step (at time t) of the plurality of iterations comprises:

computing a query vector at the current iteration by an Long-Short-Term-Memory (LSTM) model using an input to the LSTM model, the input comprising the query vector at a previous iteration step (at time t−1) and a weighted sum of a set of hidden states of each node from amongst the plurality of nodes of the molecular graph at the previous iteration step, wherein the query vector is a learnable parameter of the LSTM model;

computing an attention score ($S_{i,t}$) based on an attention function computed at the current iteration step for each node of the plurality of nodes, wherein computing the attention score at each iteration comprises:

obtaining a linear projection of each tuple $h_i^T$, $x_i^M$, wherein each tuple is represented as a concatenation of node-attributes, the node-attributes comprising the feature vector $x_i^M$ of a node i and a hidden state vector $h_i^T$ of the node i; and fusing edge information $e_{j,i}^M$ with the node-attributes by taking a product of the linear projection with the edge information to obtain an edge information fused transformed hidden state vector of the node i;

passing the edge information fused transformed hidden state vector of the node i and the query vector to the attention function to compute the attention score ($S_{i,t}$) given by:

$$S_{i,t} = f_a(e_{j,i}^M \cdot \Theta[h_i^T \| x_i^M], Q_t), \forall i \in \mathcal{V}^M$$

where $x_i^M$ ($h_i^0 = x_i^M$) denotes the feature vector of the node; and determining an attention coefficient of the node using a softmax function, wherein the softmax function is computed using the attention score of the node i with a set of neighboring nodes (j) of the node i given by: $a_{i,t} = \exp(s_{i,t})/\Sigma_{j \in \mathcal{V}}{}^M{}_{exp(s_{j,t})}$, $\forall i \in \mathcal{V}^M$, wherein the softmax function is leveraged to determine the attention coefficients of node, i at each iteration t;

computing, via the one or more hardware processors, a weighted sum ($O_t$) of the node's hidden states at the current iteration step using the weighted sum ($O_t$) of the node's (i) hidden states at the previous iteration step ($O_{t-1}$) given by:

$$O_t = \sum_{i \in \mathcal{V}^M} a_{i,t}(e_{j,i}^M \cdot \Theta[h_i^T \| x_i^M]);$$

obtaining a product of node's hidden states from the plurality of iterations to compute a graph level embedding via the one or more hardware processors determined as: $h_M^* = O_1 \odot O_2 \odot \ldots \odot O_M$, wherein the embedding $h_M^*$ is fed through a downstream multi-layer perceptron neural network to predict molecular properties of the molecular graphs; and predicting the molecular property of the molecular graph via the one or more hardware processors, by feeding the graph level embedding through the linear projection.

2. A system for molecular property prediction, comprising:

a memory storing instructions;

one or more communication interfaces; and one or more hardware processors coupled to the memory via the one or more communication interfaces, wherein the one or more hardware processors are configured by the instructions to:

access a database comprising a plurality of molecular graphs associated with a plurality of molecules and a plurality of labels indicative of chemical properties of the plurality of the molecular graphs, wherein each molecular graph of the plurality of molecular graphs comprises a plurality of nodes and a plurality of edges connecting a plurality of neighboring nodes;

map node embeddings of a molecular graph from amongst the plurality of molecular graphs to a graph-level embedding characterizing the molecular graph, wherein a graph level embedding is acquired by pooling characteristics of hidden states of the nodes in the molecular graph by performing an iterative content based attention in a plurality of iterations, wherein to pool the characteristics of hidden states of the nodes in a current iteration step (at time t) of the plurality of iterations, the one or more hardware processors are configured by the instructions to:

compute a query vector at the current iteration by an Long-Short-Term-Memory (LSTM) model using an input to the LSTM model, the input comprising a query vector at a previous iteration step (at time t−1) and a weighted sum of a set of hidden states of each node from amongst a plurality of nodes of the molecular graph at the previous iteration step, wherein the query vector is a learnable parameter of the LSTM model;

compute an attention score ($S_{i,t}$) based on an attention function computed at the current iteration step for each node of the plurality of nodes, wherein to compute the attention score at each iteration, the one or more hardware processors are configured by the instructions to:

obtain a linear projection of each tuple $h_i^T$, $x_i^M$, wherein each tuple is represented as a concatenation of node-attributes, the node-attributes comprising the feature vector $x_i^M$ of node i and hidden state vector $h_i^T$ of the node i; and fuse edge information $e_{j,i}^M$ with the node-attributes by taking a product of the linear projection with the edge information to obtain an edge information fused transformed hidden state vector of the node i;

pass the edge information fused transformed hidden state vector of node i and the query vector to the attention function to compute the attention score ($S_{i,t}$) given by:

$$S_{i,t} = f_a(e_{j,i}^M \cdot \Theta[h_i^T \| x_i^M], Q_t), \forall i \in \mathcal{V}^M$$

where $x_i^M$ ($h_i^0 = x_i^M$) denotes the feature vector of the node; and determine an attention coefficient of the node using a softmax function, wherein the softmax function is computed using the attention score of node i with a set of neighboring nodes (j) of the node i given by: $a_{i,t} = \exp(s_{i,t})/\Sigma_{j \in \mathcal{V}}{}^M \exp(s_{j,t})$, $\forall i \in \mathcal{V}^M$ wherein the softmax function is leveraged to determine the attention coefficients of node, i at each iteration t;

compute a weighted sum ($O_t$) of the node's hidden states at the current iteration step using the weighted sum ($O_t$) of the node's hidden states at the previous iteration step ($O_{t-1}$) given by:

$$O_t = \sum_{i \in \mathcal{V}^M} a_{i,t}(e_{j,i}^M \cdot \Theta[h_i^T \| x_i^M]);$$

obtain a product of node's (i) hidden states from the plurality of iterations to compute a graph level embedding determined as: $h^M* = O_1 \odot O_2 \odot \ldots \odot O_M$, wherein the embedding $h_M^*$ is fed through a downstream multi-layer perceptron neural network to predict the molecular properties of the molecular graphs; and predict the molecular properties of the molecular graph by feeding the graph level embedding through the linear projection.

3. One or more non-transitory machine-readable information storage mediums comprising one or more instructions which when executed by one or more hardware processors cause:

accessing, a database comprising a plurality of molecular graphs associated with a plurality of molecules and a plurality of labels indicative of chemical properties of the plurality of the molecular graphs, wherein each molecular graph of the plurality of molecular graphs comprises a plurality of nodes and a plurality of edges connecting a plurality of neighboring nodes;

mapping a node embedding of a molecular graph from amongst the plurality of molecular graphs to a graph-level embedding characterizing the molecular graph, via the one or more hardware processors, wherein the graph level embedding is acquired by pooling characteristics of hidden states of the nodes in the molecular graph by performing an iterative content based attention in a plurality of iterations, wherein pooling the characteristics of hidden states of the nodes in a current iteration step (at time t) of the plurality of iterations comprises:

computing a query vector at the current iteration by an Long-Short-Term-Memory (LSTM) model using an input to the LSTM model, the input comprising the query vector at a previous iteration step (at time t−1) and a weighted sum of a set of hidden states of each node from amongst the plurality of nodes of the molecular graph at the previous iteration step, wherein the query vector is a learnable parameter of the LSTM model;

computing an attention score ($S_{i,t}$) based on an attention function computed at the current iteration step for each node of the plurality of nodes, wherein computing the attention score at each iteration comprises:

obtaining a linear projection of each tuple $h_i^T$, $x_i^M$, wherein each tuple is represented as a concatenation of node-attributes, the node-attributes comprising the feature vector $x_i^M$ of a node i and a hidden state vector $h_i^T$ of the node i; and fusing edge information $e_{j,i}^M$ with the node-attributes by taking a product of the linear projection with the edge information to obtain an edge information fused transformed hidden state vector of the node i;

passing the edge information fused transformed hidden state vector of the node i and the query vector to the attention function to compute the attention score ($S_{i,t}$) given by:

$$S_{i,t} = f_a(e_{j,i}^M \cdot \Theta[h_i^T \| x_i^M], Q_t), \forall\, i \in \mathcal{V}^M$$

where $x_i^M$ ($h_i^0 = x_i^M$) denotes the feature vector of the node; and determining an attention coefficient of the node using a softmax function, wherein the softmax function is computed using the attention score of the node i with a set of neighboring nodes (j) of the node i given by:

$a_{i,t} = \exp(s_{i,t})/\Sigma_{j \in \mathcal{V}^M} \exp(s_{j,t})$, $\forall\, i \in \mathcal{V}^M$, wherein the softmax function is leveraged to determine the attention coefficients of node, i at each iteration t;

computing, via the one or more hardware processors, a weighted sum ($O_t$) of the node's hidden states at the current iteration step using the weighted sum ($O_t$) of the node's (i) hidden states at the previous iteration step ($O_{t-1}$) given by:

$$O_t = \sum\nolimits_{i \in \mathcal{V}^M} a_{i,t}(e_{j,i}^M \cdot \Theta[h_i^T \| x_i^M]);$$

obtaining a product of node's hidden states from the plurality of iterations to compute a graph level embedding via the one or more hardware processors; and predicting the molecular property of the molecular graph, by feeding the graph level embedding through the linear projection.

* * * * *